(12) United States Patent
Harrison et al.

(10) Patent No.: US 6,551,597 B1
(45) Date of Patent: Apr. 22, 2003

(54) VACCINE COMPOSITIONS FOR HUMAN PAPILLOMAVIRUS

(75) Inventors: Stephen Harrison, Cambridge, MA (US); Xiaojiang Chen, Denver, CO (US)

(73) Assignee: President & Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/520,822

(22) Filed: Mar. 8, 2000

Related U.S. Application Data (60) Provisional application No. 60/125,208, filed on Mar. 18, 1999, and provisional application No. 60/148,544, filed on Aug. 12, 1999.

(51) Int. Cl.⁷ ......................... A61K 39/12; C12P 21/06
(52) U.S. Cl. ............... 424/204.1; 424/186.1; 424/192.1; 435/69.1; 435/69.3; 536/23.72; 536/23.4
(58) Field of Search ............ 424/204.1, 186.1, 424/192.1; 435/235.1, 69.1, 69.3; 536/23.72, 23.4

(56) References Cited

U.S. PATENT DOCUMENTS 5,871,998 A * 2/1999 Lowy et al. ................. 435/235
6,228,368 B1 * 5/2001 Gissmann et al. ....... 424/204.1

FOREIGN PATENT DOCUMENTS

WO    WO 99/01557    1/1999

OTHER PUBLICATIONS

Li et al, Journal of Virology, Apr. 1997, p. 2988–2995.*
Paintsil et al, Virology, 1996, vol. 223, 238–244.*

* cited by examiner

*Primary Examiner*—Ali R. Salmi
(74) *Attorney, Agent, or Firm*—Palmer & Dodge LLP; Kathleen M. Williams (57) ABSTRACT

Large quantities of soluble multimers of human papillomavirus L1 proteins can be produced in bacterial expression systems and used as therapeutic and diagnostic tools. L1 multimers can be used in immunogenic vaccine compositions, as diagnostic reagents, and as tools for mapping cell surface receptor interactions.

9 Claims, 8 Drawing Sheets

SEQUENCE LISTING

<160> NUMBER OF SEQ ID NOS: 4

<210> SEQ ID NO 1
<211> LENGTH: 531
<212> TYPE: PRT
<213> ORGANISM: Human papillomavirus type 16

<400> SEQUENCE: 1

```
Met Gln Val Thr Phe Ile Tyr Ile Leu Val Ile Thr Cys Tyr Glu Asn
 1               5                  10                  15

Asp Val Asn Val Tyr His Ile Phe Phe Gln Met Ser Leu Trp Leu Pro
            20                  25                  30

Ser Glu Ala Thr Val Tyr Leu Pro Val Pro Val Ser Lys Val Val
        35                  40                  45

Ser Thr Asp Glu Tyr Val Ala Arg Thr Asn Ile Tyr Tyr His Ala Gly
     50                  55                  60

Thr Ser Arg Leu Leu Ala Val Gly His Pro Tyr Phe Pro Ile Lys Lys
 65                  70                  75                  80

Pro Asn Asn Asn Lys Ile Leu Val Pro Lys Val Ser Gly Leu Gln Tyr
                85                  90                  95

Arg Val Phe Arg Ile His Leu Pro Asp Pro Asn Lys Phe Gly Phe Pro
            100                 105                 110

Asp Thr Ser Phe Tyr Asn Pro Asp Thr Gln Arg Leu Val Trp Ala Cys
        115                 120                 125

Val Gly Val Glu Val Gly Arg Gly Gln Pro Leu Gly Val Gly Ile Ser
    130                 135                 140

Gly His Pro Leu Leu Asn Lys Leu Asp Asp Thr Glu Asn Ala Ser Ala
145                 150                 155                 160

Tyr Ala Ala Asn Ala Gly Val Asp Asn Arg Glu Cys Ile Ser Met Asp
                165                 170                 175

Tyr Lys Gln Thr Gln Leu Cys Leu Ile Gly Cys Lys Pro Pro Ile Gly
            180                 185                 190

Glu His Trp Gly Lys Gly Ser Pro Cys Thr Asn Val Ala Val Asn Pro
        195                 200                 205

Gly Asp Cys Pro Pro Leu Glu Leu Ile Asn Thr Val Ile Gln Asp Gly
    210                 215                 220

Asp Met Val His Thr Gly Phe Gly Ala Met Asp Phe Thr Thr Leu Gln
225                 230                 235                 240

Ala Asn Lys Ser Glu Val Pro Leu Asp Ile Cys Thr Ser Ile Cys Lys
                245                 250                 255

Tyr Pro Asp Tyr Ile Lys Met Val Ser Glu Pro Tyr Gly Asp Ser Leu
            260                 265                 270

Phe Phe Tyr Leu Arg Arg Glu Gln Met Phe Val Arg His Leu Phe Asn
        275                 280                 285

Arg Ala Gly Thr Val Gly Glu Asn Val Pro Asp Asp Leu Tyr Ile Lys
    290                 295                 300

Gly Ser Gly Ser Thr Ala Asn Leu Ala Ser Ser Asn Tyr Phe Pro Thr
305                 310                 315                 320

Pro Ser Gly Ser Met Val Thr Ser Asp Ala Gln Ile Phe Asn Lys Pro
                325                 330                 335

Tyr Trp Leu Gln Arg Ala Gln Gly His Asn Asn Gly Ile Cys Trp Gly
            340                 345                 350

Asn Gln Leu Phe Val Thr Val Val Asp Thr Thr Arg Ser Thr Asn Met
```

-continued

```
                355                 360                 365
Ser Leu Cys Ala Ala Ile Ser Thr Ser Glu Thr Thr Tyr Lys Asn Thr
    370                 375                 380

Asn Phe Lys Glu Tyr Leu Arg His Gly Glu Glu Tyr Asp Leu Gln Phe
385                 390                 395                 400

Ile Phe Gln Leu Cys Lys Ile Thr Leu Thr Ala Asp Val Met Thr Tyr
                405                 410                 415

Ile His Ser Met Asn Ser Thr Ile Leu Glu Asp Trp Asn Phe Gly Leu
            420                 425                 430

Gln Pro Pro Pro Gly Gly Thr Leu Glu Asp Thr Tyr Arg Phe Val Thr
                435                 440                 445

Gln Ala Ile Ala Cys Gln Lys His Thr Pro Pro Ala Pro Lys Glu Asp
    450                 455                 460

Asp Pro Leu Lys Lys Tyr Thr Phe Trp Glu Val Asn Leu Lys Glu Lys
465                 470                 475                 480

Phe Ser Ala Asp Leu Asp Gln Phe Pro Leu Gly Arg Lys Phe Leu Leu
                485                 490                 495

Gln Ala Gly Leu Lys Ala Lys Pro Lys Phe Thr Leu Gly Lys Arg Lys
            500                 505                 510

Ala Thr Pro Thr Thr Ser Ser Thr Ser Thr Thr Ala Lys Arg Lys Lys
        515                 520                 525

Arg Lys Leu
    530

<210> SEQ ID NO 2
<211> LENGTH: 473
<212> TYPE: PRT
<213> ORGANISM: Human papillomavirus type 16

<400> SEQUENCE: 2

Met Arg His Lys Arg Ser Ala Lys Arg Thr Lys Arg Ala Ser Ala Thr
  1               5                  10                  15

Gln Leu Tyr Lys Thr Cys Lys Gln Ala Gly Thr Cys Pro Pro Asp Ile
             20                  25                  30

Ile Pro Lys Val Glu Gly Lys Thr Ile Ala Glu Gln Ile Leu Gln Tyr
         35                  40                  45

Gly Ser Met Gly Val Phe Phe Gly Gly Leu Gly Ile Gly Thr Gly Ser
     50                  55                  60

Gly Thr Gly Gly Arg Thr Gly Tyr Ile Pro Leu Gly Thr Arg Pro Pro
 65                  70                  75                  80

Thr Ala Thr Asp Thr Leu Ala Pro Val Arg Pro Pro Leu Thr Val Asp
                 85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125

Asp Val Ser Gly Phe Ser Ile Thr Thr Ser Thr Asp Thr Thr Pro Ala
    130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190
```

Tyr Glu Glu Ile Pro Met Asp Thr Phe Ile Val Ser Thr Asn Pro Asn
                195                 200                 205

Thr Val Thr Ser Ser Thr Pro Ile Pro Gly Ser Arg Pro Val Ala Arg
            210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
                260                 265                 270

Asn Ser Ile Asn Ile Ala Pro Asp Pro Asp Phe Leu Asp Ile Val Ala
            275                 280                 285

Leu His Arg Pro Ala Leu Thr Ser Arg Arg Thr Gly Ile Arg Tyr Ser
    290                 295                 300

Arg Ile Gly Asn Lys Gln Thr Leu Arg Thr Arg Ser Gly Lys Ser Ile
305                 310                 315                 320

Gly Ala Lys Val His Tyr Tyr Tyr Asp Leu Ser Thr Ile Asp Pro Ala
                325                 330                 335

Glu Glu Ile Glu Leu Gln Thr Ile Thr Pro Ser Thr Tyr Thr Thr Thr
                340                 345                 350

Ser His Ala Ala Ser Pro Thr Ser Ile Asn Asn Gly Leu Tyr Asp Ile
            355                 360                 365

Tyr Ala Asp Asp Phe Ile Thr Asp Thr Ser Thr Thr Pro Val Pro Ser
    370                 375                 380

Val Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
                405                 410                 415

Pro Ile Asn Ile Thr Asp Gln Ala Pro Ser Leu Ile Pro Ile Val Pro
                420                 425                 430

Gly Ser Pro Gln Tyr Thr Ile Ile Ala Asp Ala Gly Asp Phe Tyr Leu
            435                 440                 445

His Pro Ser Tyr Tyr Met Leu Arg Lys Arg Arg Lys Arg Leu Pro Tyr
    450                 455                 460

Phe Phe Ser Asp Val Ser Leu Ala Ala
465                 470

<210> SEQ ID NO 3
<211> LENGTH: 568
<212> TYPE: PRT
<213> ORGANISM: Human papillomavirus type 18

<400> SEQUENCE: 3

Met Cys Leu Tyr Thr Arg Val Leu Ile Leu His Tyr His Leu Leu Pro
1               5                   10                  15

Leu Tyr Gly Pro Leu Tyr His Pro Arg Pro Leu Pro Leu His Ser Ile
                20                  25                  30

Leu Val Tyr Met Val His Ile Ile Ile Cys Gly His Tyr Ile Ile Leu
            35                  40                  45

Phe Leu Arg Asn Val Asn Val Phe Pro Ile Phe Leu Gln Met Ala Leu
    50                  55                  60

Trp Arg Pro Ser Asp Asn Thr Val Tyr Leu Pro Pro Pro Ser Val Ala
65                  70                  75                  80

Arg Val Val Asn Thr Asp Asp Tyr Val Thr Pro Thr Ser Ile Phe Tyr
                85                  90                  95

```
His Ala Gly Ser Ser Arg Leu Leu Thr Val Gly Asn Pro Tyr Phe Arg
            100                 105                 110

Val Pro Ala Gly Gly Asn Lys Gln Asp Ile Pro Lys Val Ser Ala
            115                 120                 125

Tyr Gln Tyr Arg Val Phe Arg Val Gln Leu Pro Asp Pro Asn Lys Phe
            130                 135                 140

Gly Leu Pro Asp Thr Ser Ile Tyr Asn Pro Glu Thr Gln Arg Leu Val
145                     150                 155                 160

Trp Ala Cys Ala Gly Val Glu Ile Gly Arg Gly Gln Pro Leu Gly Val
                    165                 170                 175

Gly Leu Ser Gly His Pro Phe Tyr Asn Lys Leu Asp Asp Thr Glu Ser
                180                 185                 190

Ser His Ala Ala Thr Ser Asn Val Ser Glu Asp Val Arg Asp Asn Val
            195                 200                 205

Ser Val Asp Tyr Lys Gln Thr Gln Leu Cys Ile Leu Gly Cys Ala Pro
            210                 215                 220

Ala Ile Gly Glu His Trp Ala Lys Gly Thr Ala Cys Lys Ser Arg Pro
225                 230                 235                 240

Leu Ser Gln Gly Asp Cys Pro Pro Leu Glu Leu Lys Asn Thr Val Leu
                245                 250                 255

Glu Asp Gly Asp Met Val Asp Thr Gly Tyr Gly Ala Met Asp Phe Ser
                260                 265                 270

Thr Leu Gln Asp Thr Lys Cys Glu Val Pro Leu Asp Ile Cys Gln Ser
            275                 280                 285

Ile Cys Lys Tyr Pro Asp Tyr Leu Gln Met Ser Ala Asp Pro Tyr Gly
            290                 295                 300

Asp Ser Met Phe Phe Cys Leu Arg Arg Glu Gln Leu Phe Ala Arg His
305                 310                 315                 320

Phe Trp Asn Arg Ala Gly Thr Met Gly Asp Thr Val Pro Gln Ser Leu
                325                 330                 335

Tyr Ile Lys Gly Thr Gly Met Pro Ala Ser Pro Gly Ser Cys Val Tyr
                340                 345                 350

Ser Pro Ser Pro Ser Gly Ser Ile Val Thr Ser Asp Ser Gln Leu Phe
            355                 360                 365

Asn Lys Pro Tyr Trp Leu His Lys Ala Gln Gly His Asn Asn Gly Val
            370                 375                 380

Cys Trp His Asn Gln Leu Phe Val Thr Val Val Asp Thr Thr Pro Ser
385                 390                 395                 400

Thr Asn Leu Thr Ile Cys Ala Ser Thr Gln Ser Pro Val Pro Gly Gln
                405                 410                 415

Tyr Asp Ala Thr Lys Phe Lys Gln Tyr Ser Arg His Val Glu Glu Tyr
            420                 425                 430

Asp Leu Gln Phe Ile Phe Gln Leu Cys Thr Ile Thr Leu Thr Ala Asp
            435                 440                 445

Val Met Ser Tyr Ile His Ser Met Asn Ser Ser Ile Leu Glu Asp Trp
            450                 455                 460

Asn Phe Gly Val Pro Pro Pro Thr Thr Ser Leu Val Asp Thr Tyr
465                 470                 475                 480

Arg Phe Val Gln Ser Val Ala Ile Thr Cys Gln Lys Asp Ala Ala Pro
                485                 490                 495

Ala Glu Asn Lys Asp Pro Tyr Asp Lys Leu Lys Phe Trp Asn Val Asp
            500                 505                 510
```

```
Leu Lys Glu Lys Phe Ser Leu Asp Leu Asp Gln Tyr Pro Leu Gly Arg
            515                 520                 525

Lys Phe Leu Val Gln Ala Gly Leu Arg Arg Lys Pro Thr Ile Gly Pro
        530                 535                 540

Arg Lys Arg Ser Ala Pro Ser Ala Thr Thr Ser Ser Lys Pro Ala Lys
545                 550                 555                 560

Arg Val Arg Val Arg Ala Arg Lys
                565

<210> SEQ ID NO 4
<211> LENGTH: 462
<212> TYPE: PRT
<213> ORGANISM: Human papillomavirus type 18

<400> SEQUENCE: 4

Met Val Ser His Arg Ala Ala Arg Arg Lys Arg Ala Ser Val Thr Asp
  1               5                  10                  15

Leu Tyr Lys Thr Cys Lys Gln Ser Gly Thr Cys Pro Pro Asp Val Val
             20                  25                  30

Pro Lys Val Glu Gly Thr Thr Leu Ala Asp Lys Ile Leu Gln Trp Ser
         35                  40                  45

Ser Leu Gly Ile Phe Leu Gly Gly Leu Gly Ile Gly Thr Gly Ser Gly
     50                  55                  60

Thr Gly Gly Arg Thr Gly Tyr Ile Pro Leu Gly Gly Arg Ser Asn Thr
 65                  70                  75                  80

Val Val Asp Val Gly Pro Thr Arg Pro Pro Val Val Ile Glu Pro Val
                 85                  90                  95

Gly Pro Thr Asp Pro Ser Ile Val Thr Leu Ile Glu Asp Ser Ser Val
            100                 105                 110

Val Thr Ser Gly Ala Pro Arg Pro Thr Phe Thr Gly Thr Ser Gly Phe
        115                 120                 125

Asp Ile Thr Ser Ala Gly Thr Thr Thr Pro Ala Val Leu Asp Ile Thr
    130                 135                 140

Pro Ser Ser Thr Ser Val Ser Ile Ser Thr Thr Asn Phe Thr Asn Pro
145                 150                 155                 160

Ala Phe Ser Asp Pro Ser Ile Ile Glu Val Pro Gln Thr Gly Glu Val
                165                 170                 175

Ala Gly Asn Val Phe Val Gly Thr Pro Thr Ser Gly Thr His Gly Tyr
            180                 185                 190

Glu Glu Ile Pro Leu Gln Thr Phe Ala Ser Ser Gly Thr Gly Glu Glu
        195                 200                 205

Pro Ile Ser Ser Thr Pro Leu Pro Thr Val Arg Arg Val Ala Gly Pro
    210                 215                 220

Arg Leu Tyr Ser Arg Ala Tyr Gln Gln Val Ser Val Ala Asn Pro Glu
225                 230                 235                 240

Phe Leu Thr Arg Pro Ser Ser Leu Ile Thr Tyr Asp Asn Pro Ala Phe
                245                 250                 255

Glu Pro Val Asp Thr Thr Leu Thr Phe Asp Pro Arg Ser Asp Val Pro
            260                 265                 270

Asp Ser Asp Phe Met Asp Ile Ile Arg Leu His Arg Pro Ala Leu Thr
        275                 280                 285

Ser Arg Arg Gly Thr Val Arg Phe Ser Arg Leu Gly Gln Arg Ala Thr
    290                 295                 300

Met Phe Thr Arg Ser Gly Thr Gln Ile Gly Ala Arg Val His Phe Tyr
305                 310                 315                 320
```

```
His Asp Ile Ser Pro Ile Ala Pro Ser Pro Glu Tyr Ile Glu Leu Gln
            325             330             335

Pro Leu Val Ser Ala Thr Glu Asp Asn Asp Leu Phe Asp Ile Tyr Ala
            340             345             350

Asp Asp Met Asp Pro Ala Val Pro Val Pro Ser Arg Ser Thr Thr Ser
            355             360             365

Phe Ala Phe Phe Lys Tyr Ser Pro Thr Ile Ser Ser Ala Ser Ser Tyr
    370             375             380

Ser Asn Val Thr Val Pro Leu Thr Ser Ser Trp Asp Val Pro Val Tyr
385             390             395             400

Thr Gly Pro Asp Ile Thr Leu Pro Ser Thr Thr Ser Val Trp Pro Ile
            405             410             415

Val Ser Pro Thr Ala Pro Ala Ser Thr Gln Tyr Ile Gly Ile His Gly
            420             425             430

Thr His Tyr Tyr Leu Trp Pro Leu Tyr Tyr Phe Ile Pro Lys Lys Arg
        435             440             445

Lys Arg Val Pro Tyr Phe Phe Ala Asp Gly Phe Val Ala Ala
    450             455             460
```

VACCINE COMPOSITIONS FOR HUMAN PAPILLOMAVIRUS

The present application claims priority under 35 U.S.C. §119(e) to U.S. patent application Ser. Nos. 60/125,208, filed Mar. 18, 1999 and 60/148,544, filed Aug. 12, 1999, each of which is incorporated herein in its entirety.

The invention was made using U.S. Government funds, and therefore the U.S. Government has rights in the invention.

FIELD OF THE INVENTION

The invention relates to preparation and use of viral coat proteins. In particular, the invention relates to preparations of human papillomavirus L1 protein.

BACKGROUND OF THE INVENTION

Human papillomaviruses are involved in a variety of disease states, including benign warts and cancer. There has been considerable effort to produce vaccines against human papillomaviruses, especially against types 16 and 18, which are associated with cervical cancer. Papillomaviruses contain two structural proteins that encapsidate the viral minichromosome, L1 and L2. In the virus particle, 72 pentamers of L1 form an outer shell; L2, probably one copy per L1 pentamer, is located on the inside of the L1 shell. The L1 and L2 proteins are therefore important candidates to use as immunogens. Because papillomaviruses cannot be propagated in cell culture, however, recombinant methods must be used to produce papillomavirus proteins.

Bacterial expression systems are generally effective and inexpensive ways to produce large quantities of recombinant proteins, but it has been difficult to produce large quantities of papillomavirus L1 protein in bacterial expression systems. Thus, there is a need in the art for methods of obtaining preparations of human papillomavirus L1 proteins which can be used as immunogens and as diagnostic reagents from bacterial expression systems.

SUMMARY OF THE INVENTION

It is an object of the present invention to provide stable preparations of human papillomavirus L1 protein for use as immunogens and as diagnostic tools.

One embodiment of the invention is a composition which comprises a multimer of a human papillomavirus L1 protein and a physiologically compatible carrier. As used herein, the term "L1 protein" refers to a truncated L1 polypeptide that does not include amino terminal residues 1–8 of HPV16 L1, or the corresponding structural residues of the L1 protein of other HPV subtypes.

As used herein, the term "multimer" refers to more than one L1 monomers; however, the invention is most advantageous where "multimer" refers to 5 L1 monomers (i.e., a pentamer) up to and including 60 monomers (12 pentamers).

As used herein, the term "stable" means that the preparation of L1 protein is not proteolytically degraded or denatured by proteases when placed in 10 mM salt, 0.1 mM EDTA at 10° C. for 24 hours.

Preferably, the preparation of human papillomavirus L1 protein is also soluble.

As used herein, "soluble" means that the preparation of L1 protein remains in the supernatant after centrifugation in a table-top centrifuge at 10,000 rpm for 5 minutes.

These and other objects of the invention are provided by one or more of the embodiments which are described below.

Another embodiment of the invention is a method of immunizing a human against a human papillomavirus. A composition which comprises a multimer of a human papillomavirus L1 protein is administered to a human at a dose effective to induce an immune response against the L1 protein in the human. As used herein, "effective to induce an immune response" refers to the ability to induce an antibody response to the L1 protein or to induce a CTL response to L1.

Yet another embodiment of the invention is a method of detecting the presence of antibodies against a human papillomavirus in a biological sample. A biological sample is contacted with a multimer of a human papillomavirus L1 protein. Antibodies which bind to the multimer are detected. Detection of antibodies which are bound to the multimer identifies the presence of antibodies against the human papillomavirus in the biological sample.

A further embodiment of the invention is a method of detecting a specific subtype of human papillomavirus in a biological sample. A biological sample is contacted with an antibody which specifically binds to an L1 protein of a specific subtype of human papillomavirus. L1 protein which is bound to the antibody is detected. Detection of L1 protein which is bound to the antibody identifies the presence of the specific subtype of human papillomavirus in the biological sample.

Even another embodiment of the invention is a solid support comprising a multimer of a human papillomavirus L1 protein.

Another embodiment of the invention is a solid support comprising an antibody which specifically binds to an L1 protein of a specific type of human papillomavirus.

Still another embodiment of the invention is a method of producing a soluble multimer of a human papillomavirus L1 protein which is truncated at its amino terminus. A recombinant human papillomavirus L1 protein is expressed in a bacterial host cell. The recombinant human papillomavirus L1 protein comprises amino acids 9–505 as shown in SEQ ID NO: 1. Preferably the L1 protein comprises amino acids 10–505, 11–505, 12–505, and even 13–505 as shown in SEQ ID NO:1. The recombinant human papillomavirus L1 protein is treated to remove bacterial host cell proteins. A soluble multimer of the human papillomavirus L1 protein is thereby formed.

The present invention thus provides the art with a simple and effective method of producing large quantities of human papillomavirus L1 protein. Preparations of human papillomavirus protein can be used, inter alia, as immunogens and diagnostic tools.

BRIEF DESCRIPTION OF THE DRAWINGS

FIGS. 7A–7B.

DETAILED DESCRIPTION

Figure 1:
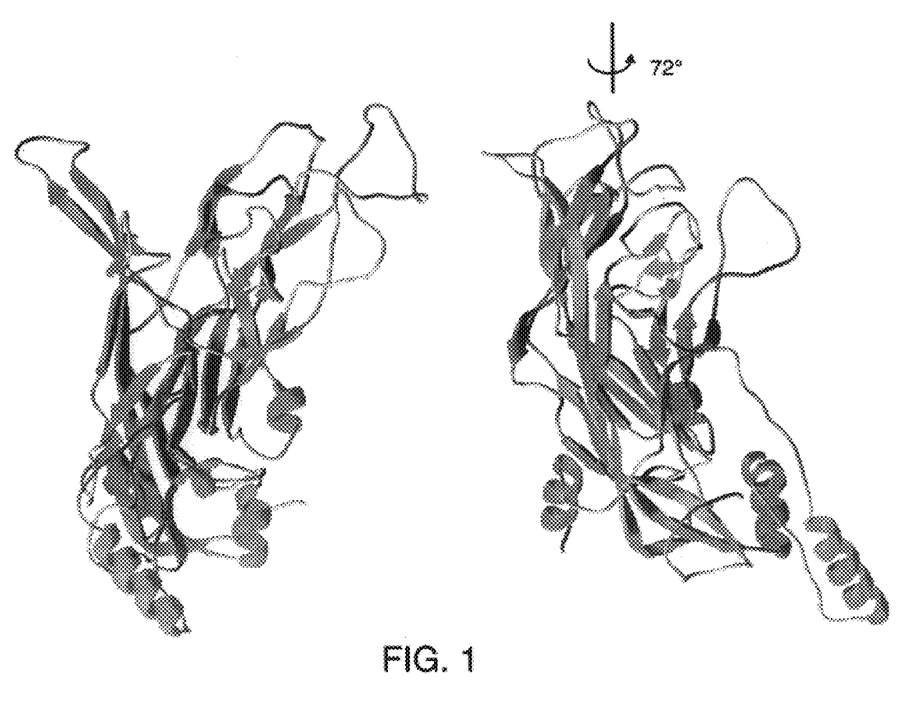
FIG. 1. Two views of the HPV 16 L1 subunit. The outward facing loops are at the top of the figure.
Figure 2:
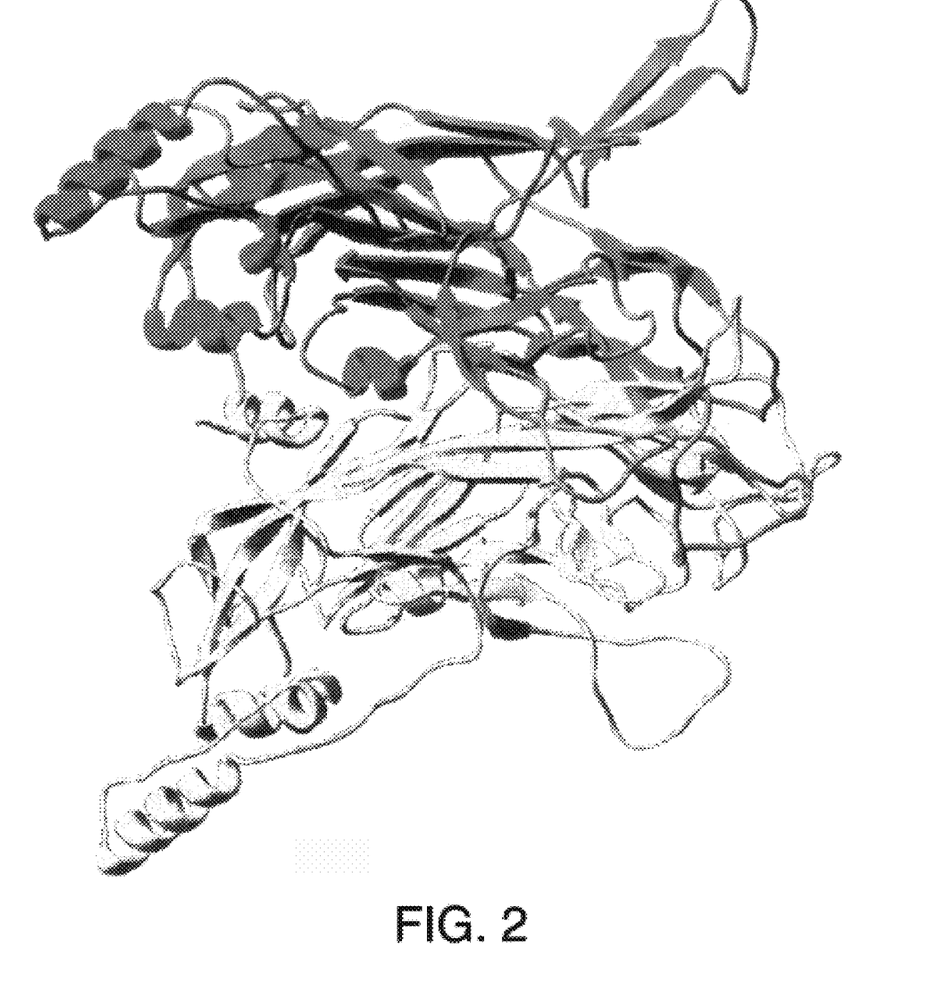
FIG. 2. Interaction between L1 monomers in a pentameric capsomere.
Figure 3:
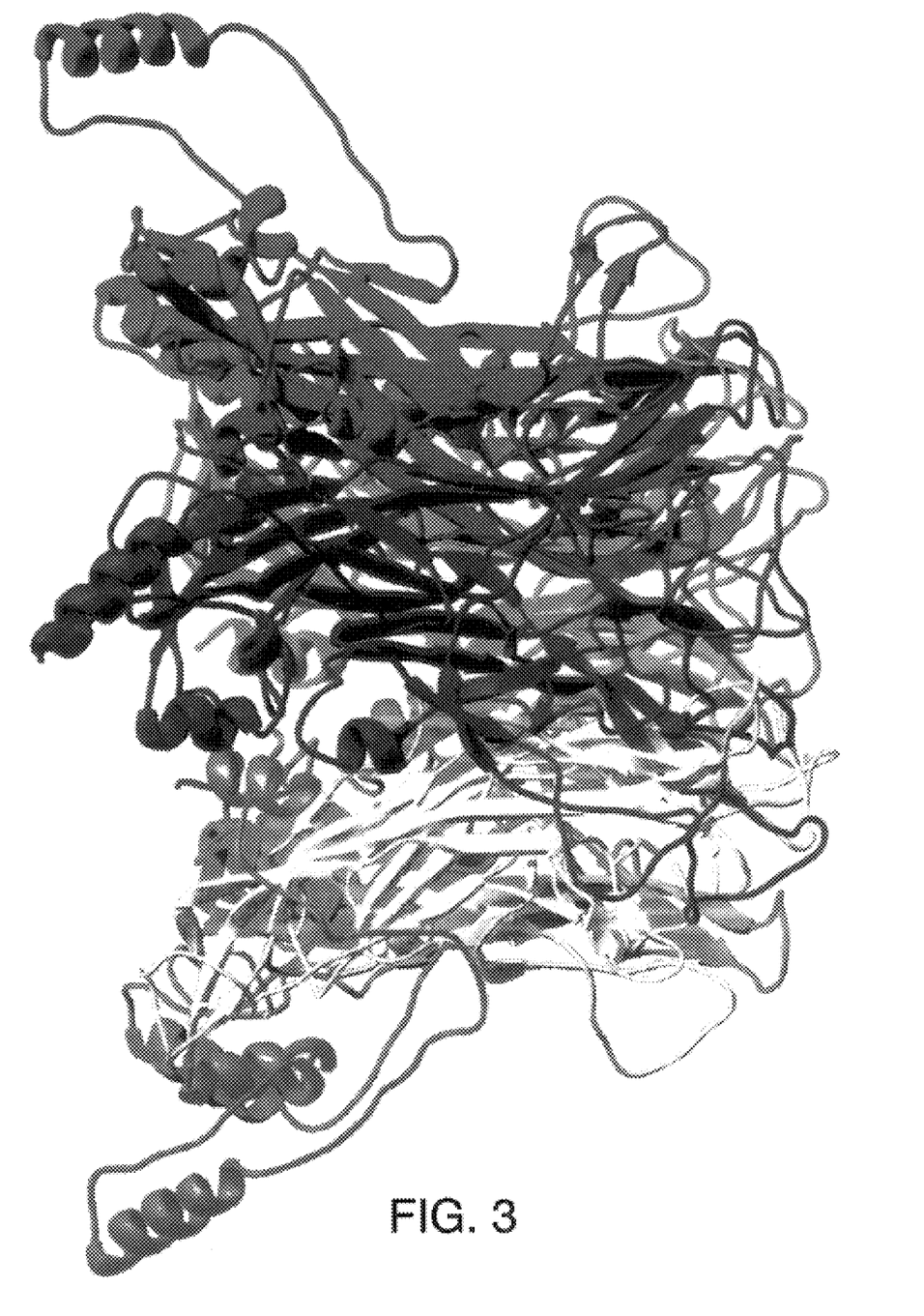
FIG. 3. A pentameric capsomere of HPV16 L1, viewed normal to the five-fold axis.
Figure 4:
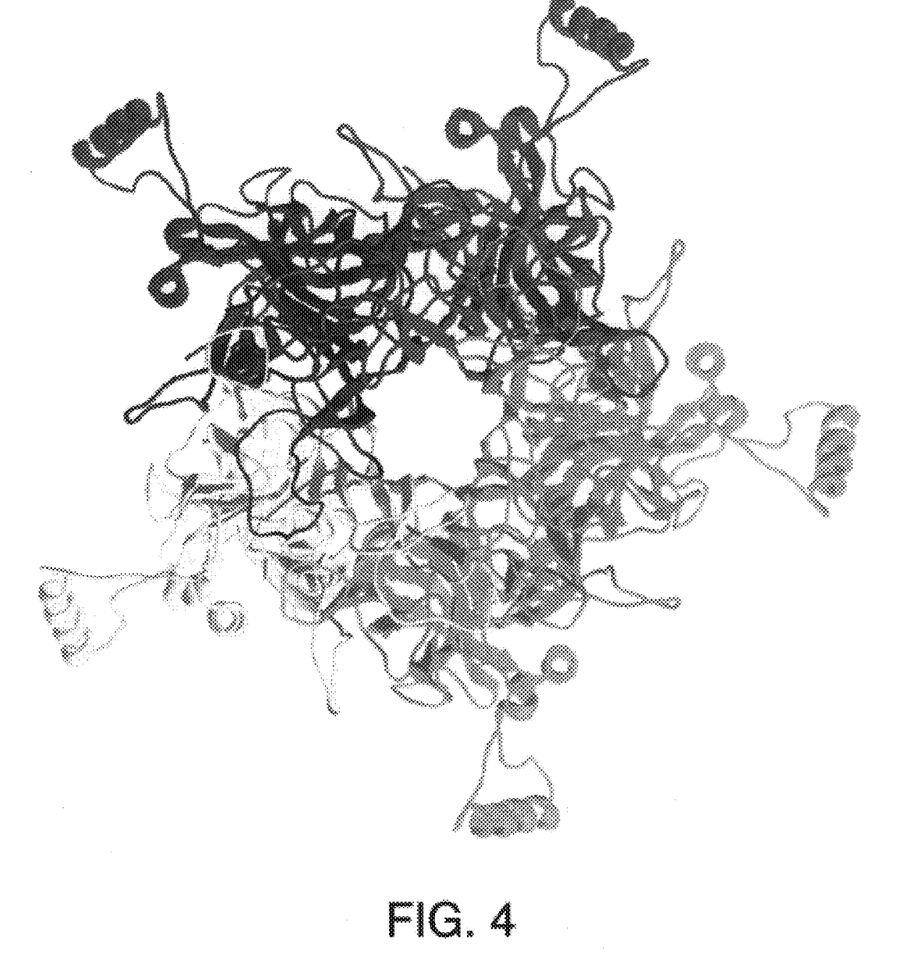
FIG. 4. View of pentameric HPV16 L1 capsomere from a direction corresponding to the outside of the icosahedral particle.
Figure 5:
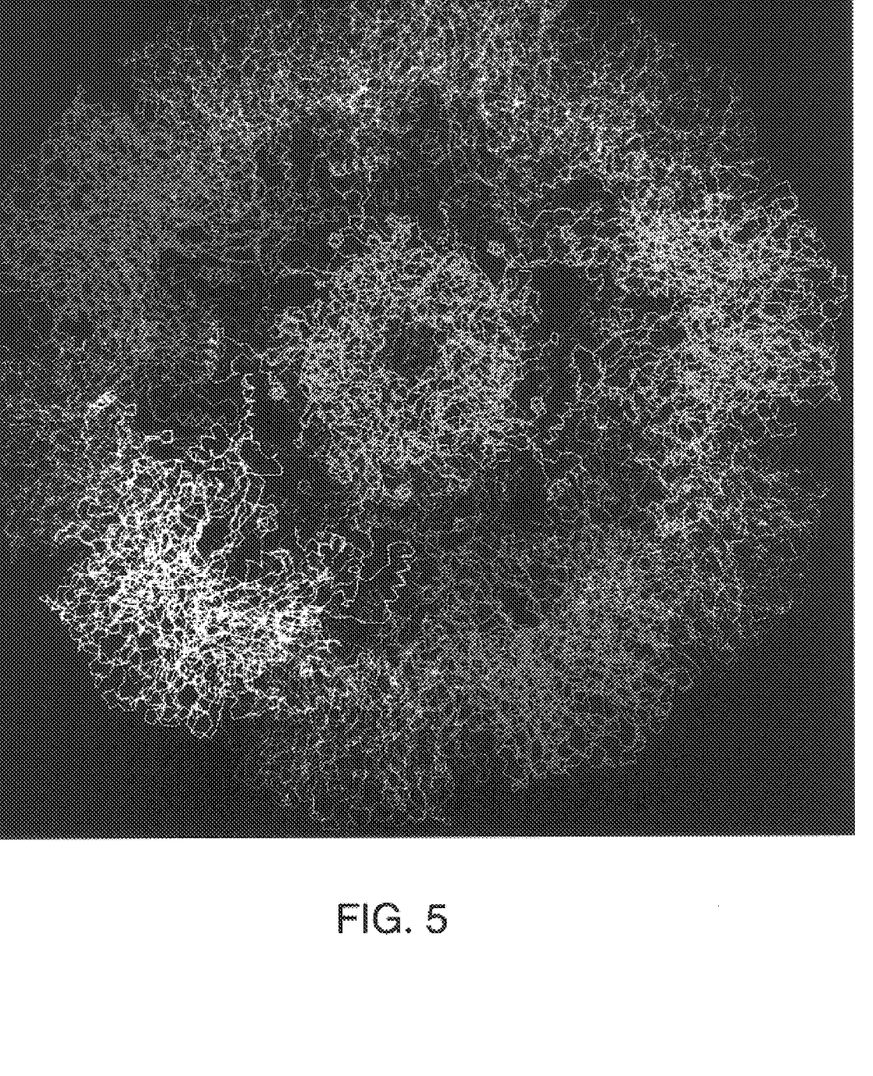
FIG. 5. The HPV16 L1 T=1 icosahedral particle.
Figure 6:
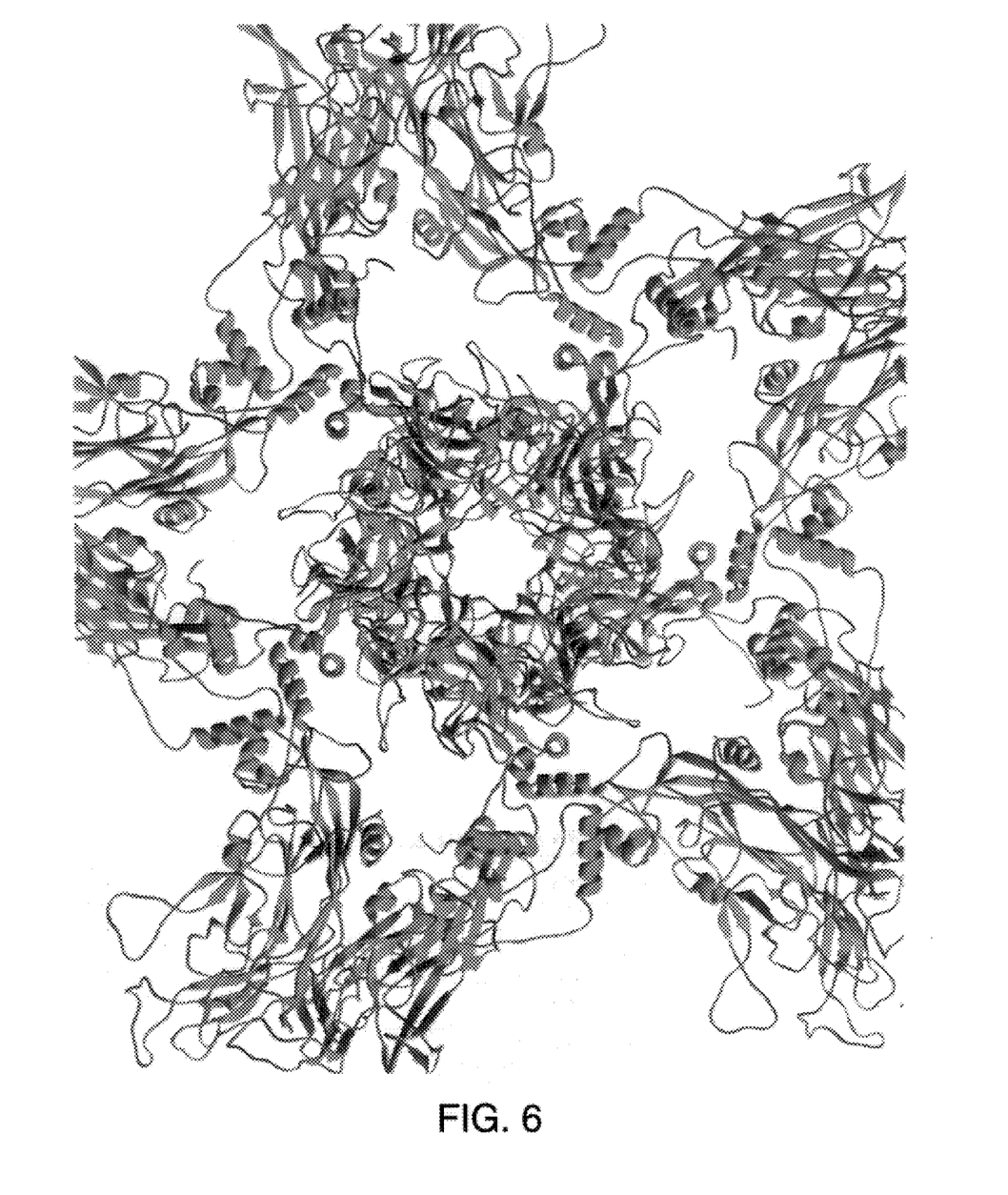
FIG. 6. Interactions between pentamers in an L1 T=1 icosahedral particle.
Figure 7A:
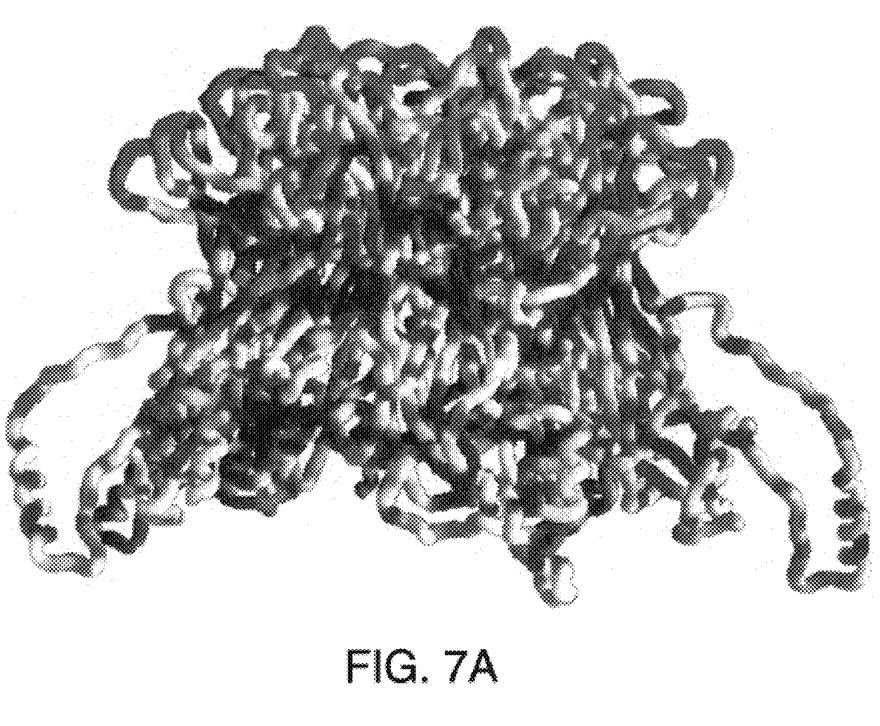
FIG. 7A, HPV16 L1 pentamer, with polypeptide chains in a worm-like representation. Positions of residues that vary significantly among HPV types are indicated by arrows.
Figure 7B:
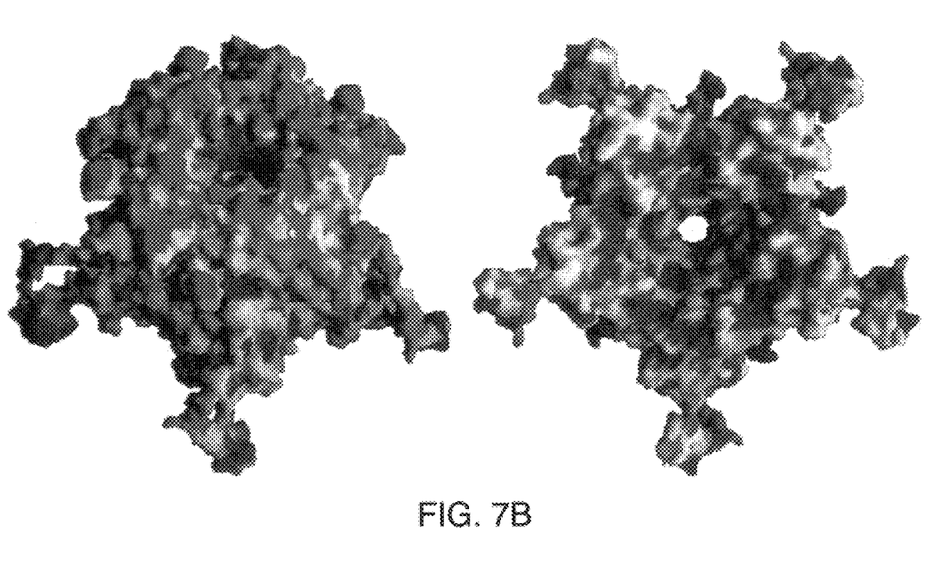
FIG. 7B, surface representation of outer (left) and inner (right) views of L1 pentamer.

It is a discovery of the present invention that L1 coat proteins of human papillomaviruses can be expressed in large quantities from bacterial host cells, particularly *E. coli* cells. The expressed L1 proteins associate to form soluble multimers. L1 multimers can be used, for example, as immunogens, to induce an immune response against human papillomavirus infection, as diagnostic tools for detecting the presence of human papillomavirus in biological samples, and as tools for mapping receptor interactions.

Multimers of Human Papillomavirus L1 Protein

An L1 multimer of the invention can comprise 2 or more, 3, 4, preferably 5, 10, 15, 20, 25, 30, 35, 40, 45, 50, or 60 or more molecules of human papillomavirus L1 protein. Pentamers of L1 protein are preferred. A 60-subunit (12-pentamer) T=1 icosahedral particle, as described below, is particularly preferred. Preferably, the multimers are soluble in an aqueous solution. Multimers of L1 protein from any human papillomavirus can be produced including, but not limited to, HPV1, HPV2, HPV3, HPV4, HPV5, HPV6, HPV7, HPV8, HPV9, HPV11, HPV12, HPV14, HPV15, HPV16, HPV17, HPV18, HPV19, HPV20, HPV21, HPV22, HPV23, HPV24, HPV25, HPV26, HPV27, HPV28, HPV29, HPV31, HPV33, HPV34, HPV35, HPV36, HPV37, HPV38, HPV42, HPV43, HPV44, HPV45, HPV51, HPV52, HPV56, HPV58, and HPV66. Optionally, an L1 multimer can comprise a molecule of human papillomavirus L2 protein from the same or from a different human papillomavirus type.

In one embodiment, the L1 molecules in the multimers are less than full-length. For example, truncated forms of human papillomavirus 16 L1 protein which lack 9, 10, 11, or 12 consecutive amino acids beginning at the amino terminus can be used to form L1 multimers. In order to be soluble, however, the expressed human papillomavirus 16 L1 proteins must comprise at least amino acids 13–505 as shown in SEQ ID NO: 1. L1 proteins from other human papillomavirus types, such as HPV 18, are also expected to be soluble with amino terminus truncations. The precise extent of the amino terminal amino acids which can be deleted will depend upon the particular amino acid sequence of the L1 protein and can be predicted by structurally aligning the L1 protein with residues of the L1 protein of HPV16. Amino acid sequences of other human papillomaviruses can be obtained, for example, from databases such as Genbank, Swiss-prot, PIR protein Data Base, PDB Protein Data Bank, or EMBL, or from the HPV sequence database, which can be accessed at <http://hpv-web.lanl.gov>. The amino acid sequences of the HPV16 and HPV18 L1 proteins are provided herein as SEQ ID NOS: 1 and 3, respectively.

L1 molecules in the multimers can comprise the natural carboxy terminus of the protein or can be truncated at the carboxy terminus by up to 30 amino acids. Again, the precise extent of the truncation will depend on the particular amino acid sequence of the L1 protein.

Icosahedral Particles

L1 multimers comprising L1 protein which is truncated at its amino terminus associate to form multimeric particles. For example, pentamers of L1 protein can associate to form 12-pentamer (60-subunit) particles with icosahedral symmetry (T=I icosahedral particles). T=1 icosahedral particles are L1 multimers which form naturally at a pH of 4–5 and a concentration of at least 0.2, 0.25, 0.3, 0.35, 0.4, 0.5, 1, 5, 10, or 20 mg/ml. Preferably, however, the T=1 icosahedral particles are stable at pH values above 4.5, such as pH 5, 5.5, 6, 6.5, or 7. Most preferably, the T=1 icosahedral particles are stable at neutral pH.

Any means known in the art which will maintain immunogenicity of the particles can be used to stabilize the particles. For example, L1 pentamers can be cross-linked to stabilize the structure of a T=1 icosahedral particle. In one embodiment, cysteine residues are introduced at particular positions in the L1 protein, to generate inter-pentamer disulfide bonds that will keep the particles assembled at higher pH values. Methods of substituting or adding codons for one or more amino acids to a coding sequence for a polypeptide are well known in the art. The positions at which cysteine residues can be introduced to result in the placement of two cysteine residues at the correct distance for formation of a disulfide bond can readily be determined by inspection of the crystal structure of the assembled L1 pentamers. Alternatively, mutations can be introduced into the L1 amino acid sequence which would improve non-covalent interactions between L1 pentamers, such as the formation of salt bridges between oppositely charged amino acids. Chemical cross-linking can also be used to stabilize the T=1 icosahedral particles.

Pentamers of L1 proteins contain outward-facing "loops" of amino acids which are clearly responsible for antigenic differences among human papillomavirus types and may also confer specificity for particular cell-surface receptors (see Example 4, below). The discovery that the outward facing loops contain most of the sequence variability (and hence type variation) and that other surfaces, as well as the hydrophobic core, are conserved can be exploited to produce antibodies and vaccines which are specific for particular types of human papillomavirus. The term "outward facing loop" refers to residues in the BC, BE, FG, and HI loops of the L1 protein. The ability of the L1 pentamers to associate to form T=1 icosahedral particles is also important for the generation of effective vaccines against human papillomavirus. The T=1 icosahedral particles are highly polyvalent and are therefore effective immunogens. Moreover, because of their polyvalency, the T=1 icosahedral particles will bind tightly to cells with the appropriate receptor. Thus, they might penetrate those cells and produce an even broader immune response, including, for example, CTL immunity as well as antibody production.

Expression of L1 Multimers in Bacterial Host Cells

Polynucleotide segments encoding human papillomavirus L1 proteins can be inserted into expression constructs using standard molecular biology techniques and used to express large quantities of L1 protein which is capable of associating to form soluble multimers. Amino acid sequences of human papillomavirus proteins, as well as nucleotide sequences which encode the proteins, can be obtained from databases such as Genbank, Swiss-prot, EMBL, PIR Protein Data Base, PDB Protein Data Bank, or from the HPV sequence database, found at <http://hpv-web.lanl.gov/>.

An L1 expression construct comprises a promoter which is functional in a chosen bacterial host cell. The skilled artisan can readily select an appropriate promoter from the large number of cell type-specific promoters known and used in the art. The expression construct can also contain a transcription terminator which is functional in the bacterial host cell. The expression construct comprises a polynucleotide segment which encodes the desired portion of the L1 protein. The polynucleotide segment is located downstream from the promoter. Transcription of the polynucleotide segment initiates at the promoter. The expression construct can be linear or circular and can contain sequences, if desired, for autonomous replication.

A variety of bacterial host cells are available and can be used to express or to propagate L1 expression constructs. Suitable bacterial host cells include strains of *E. coli* and Bacillus. Preferably, L1 protein is produced in *E. coli* cells. Expression constructs can be introduced into bacterial host cells using any standard transfer technique for bacterial cells known in the art.

To facilitate purification, the L1 protein can be expressed as a fusion protein, such as a GST fusion protein. After expression of the recombinant L1 protein from the bacterial host cells, the recombinant L1 protein is treated to remove bacterial host cell proteins. This can be accomplished using any method known in the art. When L1 protein is expressed in *E. coli* cells, the expressed protein must be treated to remove the *E. coli* protein GroEL. Treatment with 2 mM ATP and 3.5 M urea is especially effective at removing GroEL protein from the expressed L1 protein (see Example 1, below).

If inclusion of human papillomavirus L2 protein in an L1 multimer is desired, expression constructs encoding L2 can be introduced into the bacterial host cell, as described above, and used to co-express L2 protein in the cell. The amino acid sequences of L2 proteins from HPV16 and HPV18 are shown in SEQ ID NOS: 2 and 4, respectively. Amino acid sequences of other human papillomavirus L2 proteins can be found in databases such as Genbank, Swiss-prot, EMBL, PIR Protein Data Base, PDB Protein Data Bank, and the HPV sequence database at <http://hpv-web.lanl.gov/>. Alternatively, L1 and L2 proteins can be expressed from the same expression construct.

Compositions of L1 Multimers

L1 multimers of the invention, including T=1 icosahedral particles, can be used in a composition. L1 multimer compositions are useful, for example, in immunoassays, as vaccine compositions, and as tools for use in characterizing cell-surface receptors which bind to L1 proteins.

In one embodiment of the invention, the composition can consist essentially of L1 multimers without the presence of L2 molecules. Alternatively, an L1 multimer composition can consist of L1 multimers alone.

Compositions of the invention can be used as vaccine compositions, for example, to enhance or induce an immune response of a human to a human papillomavirus. Immune responses which can be enhanced or induced include both humoral and cell-mediated responses. Compositions comprising particular preparations of L1 multimers can be tested for the ability to induce an immune response using assays well known in the art. For example, a composition can be injected into a laboratory animal, such as a rat or mouse, and the animal can be monitored for the appearance of immune reactants, such as antibodies, directed against L1 protein. Alternatively, assays such as cytotoxic T lymphocyte assays can be performed to determine whether a particular composition of L1 multimers is immunogenic.

For use as a vaccine, a composition of the invention preferably comprises a multimer of a human papillomavirus L1 protein, preferably a pentamer or a T=1 icosahedral particle comprising twelve L1 pentamers which is stable at neutral pH. Stable L1 multimers are resistant to proteolytic degradation or denaturation. Optionally, the L1 multimer can include a molecule of an human papillomavirus L2 protein.

Vaccine compositions of the invention typically comprise a physiologically compatible carrier. Physiologically compatible carriers are well known to those in the art. Such carriers include, but are not limited to, a simple low salt solution which permits preservation of the integrity of the L1 protein, e.g., 10 mM NaCl, 0.1 mM EDTA, or to large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in L1 multimer compositions, for example, mineral salts such as hydrochlorides, hydrobromides, phosphates, or sulfates, as well as salts of organic acids such as acetates, proprionates, malonates, or benzoates. Compositions of the invention can also contain liquids, such as water, saline, glycerol, and ethanol, as well as substances such as wetting agents, emulsifying agents, or pH buffering agents.

Administration of L1 Multimer Compositions as Vaccines

Various methods can be used to administer an L1 multimer vaccine composition to a human, including intravenous, intramuscular, or subcutaneous injection. Vaccine compositions of the invention are administered at a dose effective to induce an immune response against the L1 protein. The particular dosages of the composition used to enhance an immune response will vary, for example, according to the L1 composition being used and the mammal to which the composition is administered. Generally, about 5 µg to about 50 µg of L1 multimers per kg of patient body weight, about 50 µg to about 5 mg/kg, about 100 µg to about 500 µg/kg, or about 200 to about 250 µg/kg will be administered to an adult human.

Such ranges by no means preclude use of a higher or lower amount of a component, as might be warranted in a particular application. For example, the actual dose and schedule may vary depending on whether the compositions are administered in combination with other pharmaceutical compositions, or depending on individual differences in pharmacokinetics, drug disposition, and metabolism.

Diagnostic Assays

Because of the polyvalency of L1 multimers, particularly the T=1 icosahedral particles, L1 multimers of the invention can be used to produce antibodies which specifically bind to human papillomavirus L1 proteins. Taking advantage of the high variability of the outward-facing loops of L1 pentamers, for example, antibodies can be generated which can distinguish among L1 proteins of different human papillomaviruses. These antibodies can be used, for example, in diagnostic assays, to detect directly the presence of human papillomavirus or specific types of human papillomavirus associated with a particular disease state in a biological sample. Similarly, L1 multimers themselves can be used in immunoassays, to detect the presence of antibodies to human papillomavirus in a biological sample. Use of type-specific antibodies or L1 multimers represents a significant improvement over immunoassays which use polyclonal antisera directed against a prototype human papillomavirus.

Polyclonal or monoclonal antibodies, including single-chain antibodies, which specifically bind to L1 proteins can be constructed using techniques well known in the art. Preferably, antibodies which specifically bind to human papillomavirus L1 proteins do not bind to human papillomavirus L2 proteins or to human proteins. Most preferably, the antibodies specifically bind to a specific type of human papillomavirus, such as HPV 16, HPV 18, or any of the other specific types of human papillomavirus disclosed above. Antibodies which specifically bind to L1 proteins typically do not detect other proteins in immunochemical assays and can immunoprecipitate an L1 protein or multimer from solution.

Immunoassays which can be used to detect binding of L1 proteins and antibodies include, but are not limited to, Western blots, ELISAs, radioimmunoassays, immunohistochemical assays, immunoprecipitations, or other immunochemical assays known in the art. Typically, such assays provide a detection signal at least 5-, 10-, or 20-fold higher than a background signal. Optionally, either the antibody or the L1 multimer can comprise a detectable label, such as a fluorescent, chemiluminescent, or enzymatic tag or a radiolabel.

An antibody or an L1 multimer can be bound to a solid support, such as a glass or plastic slide, tissue culture plate, microtiter well, tube, column, column matrix, protein, or particle such as a bead, including but not limited to a latex, polystyrene, or glass bead, or a flexible membrane, such as a nitrocellulose or nylon membrane. Means of coupling protein moieties to such surfaces are well known in the art, and any coupling means which does not destroy the ability of an antibody and an L1 protein to bind to each other can be used.

A biological sample to be tested is contacted with the antibody or L1 multimer. The biological sample can be any sample suspected of comprising a human papillomavirus, such as a biopsy, smear, or tissue section of a tissue such as skin, cervix, anogenital epithelium, larynx, upper respiratory tract, conjunctiva, or tissues of the oral cavity.

The following examples are provided for exemplification purposes only and are not intended to limit the scope of the invention.

EXAMPLE 1

Expression of Soluble Human Papillomavirus L1 Pentamers

We expressed the L1 protein of human papillomavirus type 16 (HPV 16) as a recombinant product in *E. coli*. Specifically, we observed that a form containing residues 10 to 505 (where 505 is the C-terminus of L1 ) is soluble when overexpressed from a tac promoter in *E. coli* strain XA90. Soluble L1 protein remains in the supernatant after centrifugation in a table-top centrifuge at 10,000 rpm for 5 minutes. Forms that start C-terminal to residue 13 are not soluble.

The L1 protein was overexpressed as a GST fusion protein, in which the GST segment of the fusion protein was coupled to the L1 segment using a protease sensitive site. A large fraction of the overexpressed L1 fusion protein is complexed with GroEL (an *E. coli* protein that is known to aid in folding) in a non-native state. To purify the fusion protein from the GroEL protein, cell lysates were treated with 2 mM ATP, 3.5 M urea, and 5 mM $MgCl_2$. The cell lysate was then applied to a glutathione column and washed with 2.3 M urea to remove any additional GroEL. After the column was washed with buffer, a protease was added to cleave the protease sensitive site of the fusion protein. The L1 protein was then eluted from the column and further purified by gel filtration. This procedure yielded homogeneous, soluble L1 pentamers.

EXAMPLE 2

Crystallization of L1 Pentamers

Crystallization trials, using a standard variation of precipitants, pH, ionic strength, etc., resulted in crystals at low pH. Several crystal forms were obtained; all turned out to have unusually large unit cells, showing that we had crystallized an assembly of L1 pentamers.

X-ray crystallographic structure determination revealed that the assembly is a 12-pentamer (60-subunit) particle with icosahedral symmetry. Thus, under the crystallization conditions, a "small icosahedral particle" or "T=1 particle" is formed. Electron microscopy of the particles demonstrated that the T=1 icosahedral particle forms in solution at low pH (pH 4–5), at concentrations of L1 pentamer of 0.2 mg/ml or greater. Forms of L1 that start at the authentic N-terminus or that start before amino acid residue 10 do not form crystallizable T=1 icosahedral particles.

EXAMPLE 3

Structure of the L1 Pentamers

The structure of the L1 pentamer, assembled into T=1 icosahedral particles, was revealed by X-ray crystallography. The L1 subunit folds into a beta-roll domain, as found in many virus structures. The arrangement of the subunits in the pentamer resembles what has been seen in the pentamers of VP1 from SV40 and polyomavirus.

A segment of the polypeptide chain of one subunit (the segment denoted strand "G1") contributes to a beta sheet (the "C-H-E-F" sheet) in the clockwise-related neighbor (viewed from the "outside" surface of the pentamer). The shape and packing of the subunits is such that the body of the pentamer resembles a pentagonal prism, with a conical hollow along the 5-fold axis that opens "inward" (that is, toward the surface that would face inward in the virus particle) and closes down to a diameter of about 12 angstroms at its narrowest point.

The C-terminal residues of each subunit project away from the body of the pentamer and interact with C-terminal residues from other pentamers around the icosahedral threefold axis of the T=1 particle. In SV40 and polyomavirus, the C-terminal 60–70 residues of each VP1 subunit project away from the body of the pentamer and "invade" neighboring pentamers, effectively tieing the virus particle together. In the HPV16 T=1 icosahedral particles we have crystallized, the C-terminally projecting arms do not invade other pentamers, but rather fold back into the subunit from which they emanated. It is possible that in the 72-pentamer shell of the HPV 16 virion, the C-terminal arms in fact "invade" neighboring pentamers, as in SV40 and polyoma. At least at low pH, the papilloma L1 C-terminal arms do not "dangle" but rather "return" to their subunit of origin, so they form anchored projections that can interact in a threefold way to stabilize the T=1 particles.

EXAMPLE 4

Conserved and Non-Conserved Residues

We have examined the amino acid sequences of 49 different HPV types. The most variable amino-acid positions are in the various loops that project from the outward-facing surface of the L1 pentamer. The core of each subunit, the residues facing the lateral walls of the pentamer, and the residues facing the conical hollow and its constriction near the outside of the pentamer are all highly conserved. We believe that the conical hollow is the binding site for the other structural protein, L2 (by analogy with our results with polyoma VP2 and VP1) and that the conservation of residues that face into it has to do with a conserved L2 interaction.

The high variability of the outward-facing loops is clearly responsible for antigenic differences among HPV types and may also confer specificity for particular cell-surface receptors. There is a pocket at the outward-facing surface of the pentamer that might be a receptor interaction site, because its position is homologous to the position of the known receptor-binding site on polyoma VP1.

What is claimed is:

1. A composition comprising:
a multimer of a human papillomavirus L1 protein, comprising at least 10 human papillomavirus L1 protein monomers assembled into at least 2 pentamers, wherein the L1 protein does not include amino terminal residues 1–8; and a pharmacologically acceptable carrier.

2. The composition of claim 1 wherein multimers of the human papillomavirus L1 protein form a T=1 icosahedral particle.

3. The composition of claim 2 wherein the T=1 icosahedral particle is stable at a pH above 4.5.

4. The composition of claim 3 wherein the T=1 icosahedral particle is stable at neutral pH.

5. The composition of claim 4 wherein the T=1 icosahedral particles are held together by means of cross-linking between the L1 pentamers.

6. The composition of claim 5 wherein the T=1 icosahedral particles are held together by means of at least one disulfide bond.

7. The composition of claim 1, wherein the multimer of the human papillomavirus L1 protein comprises a human papillomavirus L2 protein.

8. The composition of claim 1 wherein the human papillomavirus is selected from the group consisting of HPV1, HPV2, HPV3, HPV4, HPV5, HPV6, HPV7, HPV8, HPV9, HPV11, HPV12, HPV14, HPV15, HPV16, HPV17, HPV18, HPV19, HPV20, HPV21, HPV22, HPV23, HPV24, HPV25, HPV26, HPV27, HPV28, HPV29, HPV31, HPV33, HPV34, HPV35, HPV36, HPV37, HPV38, HPV42, HPV43, HPV44, HPV45, HPV5 1, HPV52, HPV56, HPV58, and HPV66.

9. The composition of claim 1 wherein the human papillomavirus is a human papillomavirus 16.

* * * * *

UNITED STATES PATENT AND TRADEMARK OFFICE
CERTIFICATE OF CORRECTION

PATENT NO.      : 6,551,597 B1
DATED           : April 22, 2003
INVENTOR(S)     : Harrison et al.

It is certified that error appears in the above-identified patent and that said Letters Patent is hereby corrected as shown below:

<u>Column 1,</u>
Line 11, please insert the following paragraph immediately before "FIELD OF THE INVENTION":
-- GOVERNMENT SUPPORT
This invention was sponsored by NIH Grant No. CA13202 and the government has certain rights to the invention. --

Signed and Sealed this

Eighth Day of July, 2003

JAMES E. ROGAN
*Director of the United States Patent and Trademark Office*